US012773150B2

(12) United States Patent
Franck

(10) Patent No.: US 12,773,150 B2
(45) Date of Patent: Oct. 27, 2026

(54) MINIMIZING COMMON MODE INTERFERENCE IN A PHYSIOLOGICAL MEASUREMENT DEVICE

(71) Applicant: KONINKLIJKE PHILIPS N.V., Eindhoven (NL)

(72) Inventor: Christoph Florian Franck, Magstadt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 560 days.

(21) Appl. No.: 18/029,994

(22) PCT Filed: Sep. 27, 2021

(86) PCT No.: PCT/EP2021/076450
§ 371 (c)(1),
(2) Date: Apr. 3, 2023

(87) PCT Pub. No.: WO2022/073781
PCT Pub. Date: Apr. 14, 2022

(65) Prior Publication Data
US 2024/0215895 A1 Jul. 4, 2024

(30) Foreign Application Priority Data
Oct. 7, 2020 (EP) .................................... 20200589

(51) Int. Cl.
*A61B 5/308* (2021.01)
*A61B 5/00* (2006.01)
*A61B 5/305* (2021.01)

(52) U.S. Cl.
CPC .............. *A61B 5/308* (2021.01); *A61B 5/305* (2021.01); *A61B 5/725* (2013.01); *A61B 2560/0223* (2013.01)

(58) Field of Classification Search
CPC ......... A61B 5/308; A61B 5/307; A61B 5/305; A61B 5/31; A61B 5/30; A61B 5/24;
(Continued)

(56) References Cited

U.S. PATENT DOCUMENTS 5,627,799 A * 5/1997 Hoshuyama ........... H04R 3/005 367/901
2008/0243021 A1* 10/2008 Causevic ............. A61B 5/4821 600/544

(Continued)

FOREIGN PATENT DOCUMENTS

WO 2018162365 A1 9/2018

OTHER PUBLICATIONS

Cox et al. "Robust Adaptive Beamforming", Oct. 1987, IEEE Transactions on Acoustics, Speech, and Signal Processing, vol. ASSP-35, No. 10, pp. 1365-1376. (Year: 1987).*

(Continued)

*Primary Examiner* — Mohamed Charioui
(74) *Attorney, Agent, or Firm* — Brynne J. Corcoran

(57) ABSTRACT

The present invention relates to a physiological measurement device (11). In order to reduce common mode interference and/or to improve characteristics of the digital input filters (11) of the measurement device (11) without compromising common mode rejection capabilities of the input filters, it is proposed to calculate by means of optimization a set of filter coefficients for at least one digital input filter (31) associated with a specific input channel of the measurement device (11) based on samples ($c_i$) of multiple input signals ($s_i$) of the measurement device (11) corresponding to a test signal (TS) applied to multiple input channels of the measurement device (11) and on at least one definition vector ($v_j$) describing a linear combination of samples ($c_i$) of at least two input channels.

15 Claims, 4 Drawing Sheets

(58) Field of Classification Search
CPC ......... A61B 5/00; A61B 5/725; A61B 5/7235; A61B 5/72; A61B 2560/0223; A61B 2560/02; A61B 2560/00; A61B 5/7225; A61B 5/341; A61B 5/339; A61B 5/318; A61B 5/316
See application file for complete search history.

(56) References Cited

U.S. PATENT DOCUMENTS

| | | | | |
|---|---|---|---|---|
| 2009/0022336 | A1* | 1/2009 | Visser | G10L 21/0272 381/94.7 |
| 2009/0304203 | A1* | 12/2009 | Haykin | H04R 25/407 381/94.1 |
| 2011/0319777 | A1* | 12/2011 | Mehrotra | A61B 5/0006 600/509 |
| 2017/0143275 | A1* | 5/2017 | Levin | A61B 5/296 |
| 2019/0200886 | A1* | 7/2019 | Welsh | A61B 5/291 |

OTHER PUBLICATIONS

International Search Report Dated Jan. 4, 2022 For International Appln No. PCT/EP2021/076450 Filed Sep. 27, 2021.

"Texas Instruments ADS1298 datasheet," [Online]. Available: https://www.ti.com/lit/ds/symlink/ads1298.pdf?ts=1591687373761&ref_url=https://www.ti.com/product/ADS1298.

T. Brand, "Increasing the Common-Mode Rejection Ratio of Differential Amplifiers Through Precisely Matched Resistor Networks," [Online]. Available: https://www.analog.com/en/technical-articles/increasing-the-common-mode-rejection-ratio-of-differential-amp.html.

"Analog Devices ADAS1000," [Online]. Available: https://www.analog.com/en/products/adas1000.html.

M. F. Santosh I. Patel and M. C. F. Michael J. Souter, "Equipment-related Electrocardiogramtifacts: Causes, Characteristics, Consequences, and Correction," Anesthesiology, 2008.

ANSI/AAMI/IEC 60601-2-25:2011/(R)2016, Medical electrical equipment—Part 2-25: Particular requirements for the basic safety and essential performance of electrocardiograma.

L. V. Stephen Boyd, Convex optimization, Cambridge University Press, 2004. https://web.stanford.edu/~boyd/cvxbook/.

"Texas Instruments ADS1298," [Online]. Available: https://www.ti.com/product/ADS1298.

* cited by examiner

MINIMIZING COMMON MODE INTERFERENCE IN A PHYSIOLOGICAL MEASUREMENT DEVICE

CROSS-REFERENCE TO PRIOR APPLICATIONS

This application is the U.S. National Phase application under 35 U.S.C. § 371 of International Application No. PCT/EP2021/076450, filed on Sep. 27, 2021, which claims the benefit of European Application No. 20200589.8 filed on Oct. 7, 2020. These applications are hereby incorporated by reference herein.

FIELD OF THE INVENTION

The present invention relates to a physiological measurement device, in particular an electrophysiological measurement device like an electrocardiographic (ECG) or an electroencephalography (EEG) device.

BACKGROUND OF THE INVENTION

Physiological measurement devices usually present measurement results to their users, e.g. medical personnel, in the form of differential value—often referred to as “vectors” or, in particular in the context of ECG or EEG, as “leads”. The differential values are derived from the difference of physical quantities measured at different points on a patient’s body. The measurement devices are designed to suppress a common mode component of signal measured at the different points as good as possible.

In WO 2018/162365, a physiological measurement device is described that includes digital filters arranged at outputs of different Analog-to-Digital Converters (ADCs) associated with different channels of the measurement device. The filters are calibrated for reduced common mode interference. A respective calibration method comprises determining a reference input channel and minimizing time-domain differences between the reference input channel and each input channel other than the reference input channel.

SUMMARY OF THE INVENTION

It is an object of the present invention to further reduce common mode interference and/or to improve characteristics of the digital filters without compromising common mode rejection capabilities of the input filters.

In a first aspect of the present invention a method for minimizing common mode interference in a physiological measurement device is presented, the method comprising receiving samples of multiple input signals of the measurement device corresponding to a test signal applied to multiple input channels of the measurement device; inputting at least one definition vector describing a linear combination of samples of at least two input channels; optimizing a metric calculated from at least one vector signal, the vector signal being based on the samples of at least two of the received input signals and the definition vector; and based on the optimizing, obtaining at least one set of filter coefficients for at least one digital input filter associated with a specific input channel. By optimizing the metric not only based on the samples of the input signal but also on the definition vectors, the selection of a reference signal can be omitted, thereby yielding well-suited sets of filter coefficients for the individual digital input filters that allows for good common-mode interference mitigation and has particularly low adverse effect with the quality of desired, e.g. differential, component of a vector signal.

The method may be a calibration method for calibrating a measurement device. The method may be executed during a production final test applied to a measurement device. However, the method is not limited to a certain use case. For example, the method can be used for performing a self test or self calibration of a measurement device. It is also possible to use the method in the course of routine maintenance tasks or the like.

In typical applications the measurement device to be calibrated has multiple leads corresponding to multiple vector signals. Accordingly, multiple definition vectors may be inputted and at least one set of filter coefficient may be obtained for a specific vector. In other words, different sets of filter coefficients may be used for the same input channel but for different vector signals. In an embodiment, a dedicated set of filter coefficients related to all filters associated with channels used by a certain vector signal may be assigned to this vector signal. Using different sets of filter coefficients for different vector signals not only allows for improved common-mode interference reduction but also simplifies the optimization in terms of computational complexity.

Another approach for keeping the computational complexity of the optimization low includes splitting the optimization into multiple optimization steps. In particular, optimizing the metric may comprises multiple optimizing steps, a set of filter coefficients obtained by one step being kept as constant for a subsequent optimizing step.

Thanks to basing the optimization on both the samples of the input signals as well on the definition vectors, constraints may be defined to control characteristics of at least one input filter which may not or not directly related with common-mode interference reduction. For example, the optimizing may subject to at least one linear equality constraint with respect to a filter coefficient. Such linear equality constraints may be applied to obtain a certain DC gain or a certain gain at the Nyquist frequency.

The method may comprise inputting a DC gain value of at least one input channel and determining a corresponding linear equality constraint based on the DC gain value. When setting the DC gain of one, multiple, or all, digital input filters based on the inputted DC gain values, differences between the channels can be compensated. In an embodiment, the DC gain value of one input channel is input and a corresponding linear equality constraint may be determined based on that single DC gain value. The DC gain value may be determined by a separate measurement process performed prior to the present method or in parallel to the present method. Applying at least one linear equality constraint, e.g. based on the DC gain value, prevents the optimizing operation form arriving at a trivial solution that minimizes the target function by simply setting all filter coefficients to zero.

Moreover, the optimizing may be subject to at least one nonlinear inequality constraint for limiting a gain of a certain input filter at a given frequency. Such constraint(s) allow to control the frequency response of the digital input filter at least to some extent. These constraints may be defined such that an undesired frequency response, e.g. of parts of an analog frontend, can be at least partly compensated.

The optimizing may also be subject to at least one bounds constraint with respect to filter coefficients. Such constraints limiting the range of the filter coefficients may avoid numerical overflows when storing the filter coefficients according to a specific digital format (e.g. a certain floating point format or a certain fixed point format). Such constraints further may limit the gain of a specific input filter at a certain frequency, e.g. to avoid amplification of unimportant frequency ranges.

The samples may be received with a calibration sampling rate that is increased compared to an operating sampling rate applied to perform physiological measurements by the measurement device and/or a calibration resolution of the received samples may differ from, preferably be less than, a measurement resolution of samples received to perform the physiological measurement. The so adapted sampling rate and/or resolution is well-suited for calibration because higher frequencies can be considered more accurately, whereas a lower resolution may be acceptable during calibration because the amplitude of the test signal can be better controlled than the amplitude of measured signals captured during normal operation of the measurement device.

Optimizing the metric may comprise minimizing a penalty function of output samples, the output samples corresponding to at least one vector signal calculated from the input signal filtered with the at least one input filter and from the vector. The vector signal corresponding to a differential measurement is often also referred to as "vector". Moreover, the test signal applied during calibration may be the same at all input channels. Accordingly, a pure common-mode signal is applied to the channels of the measurement device. Minimizing the norm of at least one vector signal then corresponds to maximizing common-mode reduction. The output samples may correspond to a single, multiple or all vector signals supported by the measurement device. When using dedicated sets of filter coefficients for the individual vector signals or for predefined groups of multiple vector signals, the output samples may correspond to the respective vectors signal or to the respective group of vectors signals.

Optimizing may comprise to minimizing multiple penalty functions of the output samples simultaneously or minimizing a scalar target function of different penalty functions. In other words, the optimization may be a multi-object optimization.

At least one penalty function may be a convex or quasi-convex penalty function, preferably a norm. For example, the 1-infinity (maximum) norm and another norm, preferably the 12 (Euclidean) norm may be minimized simultaneously or based on the scalar target function. At least one penalty function may comprise the Huber loss function.

It also possible that optimizing comprise minimizing a scalar target function of different norms or other penalty functions to reduce the computational complexity of the optimization. Composing a target function from several different norms or penalty functions may allow to achieve multiple objectives or trade off different objectives against each other. For example using a weighted sum of the 1-infinity norm and the 1-2 norm would minimize the maximum deviation (quantified by the 1-infinity norm) but also the energy content of an error signal (quantified by the 12 norm) with the balance of the trade off given by the weight.

In a further aspect of the present invention a computer program is presented. The computer program may comprise program code programmed for causing a computer, e.g. a processing unit of a device, to carry out the method. The computer program may be part of a computer program product like a computer readable non-transitory recording medium comprising the program. The computer may comprise a processing unit of a calibration device. The computer, in particular the processing unit of the calibration device, may include Input/Output (IO) circuitry configured for performing IO operations to access data present in the measurement device and/or to control the measurement device to carry out a herein described method.

In yet a further aspect of the present invention, a calibration device for minimizing common mode interference in a physiological measurement device is presented, the calibration device comprising a processing unit configured for receiving samples of multiple input signals of the measurement device corresponding to a test signal applied to multiple input channels of the measurement device; inputting at least one definition vector describing a linear combination of samples of at least two input channels; optimizing a metric calculated from at least one vector signal, the vector signal being based on the samples of at least two of the received input signals and the definition vector; and based on the optimizing, obtaining at least one set filter coefficients for at least one digital input filter associated with a specific input channel. The calibration device may be implemented as a separate device with respect to the physiological measurement device. Such separate measurement device can be used for production final tests. Alternatively, the calibration device may be adapted for integration into the physiological measurement device to provide the physiological measurement device with self test and/or self calibration functionality. In any case, the calibration device, in particular the processing unit thereof, may be configured for carrying out the above-described method.

In a further aspect of the present invention, a physiological measurement device is presented, the device comprising multiple input channels for processing multiple, typically analog, input signals; a memory device configured to store multiple sets of filter coefficients, at least one of said multiple sets being related to at least one digital input filter of the measurement device, the input filter being configured to filter samples of one input signal to obtain filtered samples of this input signal, and a processing unit configured to calculate multiple vector signals, one of said multiple vector signals being calculated from multiple filtered input signals based on a definition vector; wherein the memory device is configured to store different sets of filter coefficients related to one, in other words the same, input channel and the processing unit is configured to select one of the different sets of filter coefficient for calculating a specific vector signal. In an implementation, multiple vector signals may be defined and the memory device is configured to store the different sets of filter coefficients for one input channel, wherein at least some, preferably each, of the stored sets of filter coefficients are associated with a different one of the multiple vector signals.

In a further aspect of the present invention, a physiological measurement method is presented, the method comprising processing multiple, preferably analog, input signals via multiple input channels; storing in a memory device multiple sets of filter coefficients, at least one of said multiple sets being related to at least one digital input filter of the measurement device, the input filter being configured to filter samples of one input signal to obtain filtered samples of this input signal, and calculating multiple vector signals, one of said multiple vector signals being calculated from multiple filtered input signals based on a definition vector; wherein different sets of filter coefficients related to one input channel are stored in the memory device and one of the different sets of filter coefficient is selected for calculating a specific vector signal.

In yet further aspects of the present invention, there are provided a computer program corresponding to the measurement method which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

It shall be understood that the claimed method, system, computer program and medium have similar and/or identical preferred embodiments as the claimed system, in particular as defined in the dependent claims and as disclosed herein.

BRIEF DESCRIPTION OF THE DRAWINGS

These and other aspects of the invention will be apparent from and elucidated with reference to the embodiment(s) described hereinafter. In the following drawings.

DETAILED DESCRIPTION OF EMBODIMENTS

Figure 1:
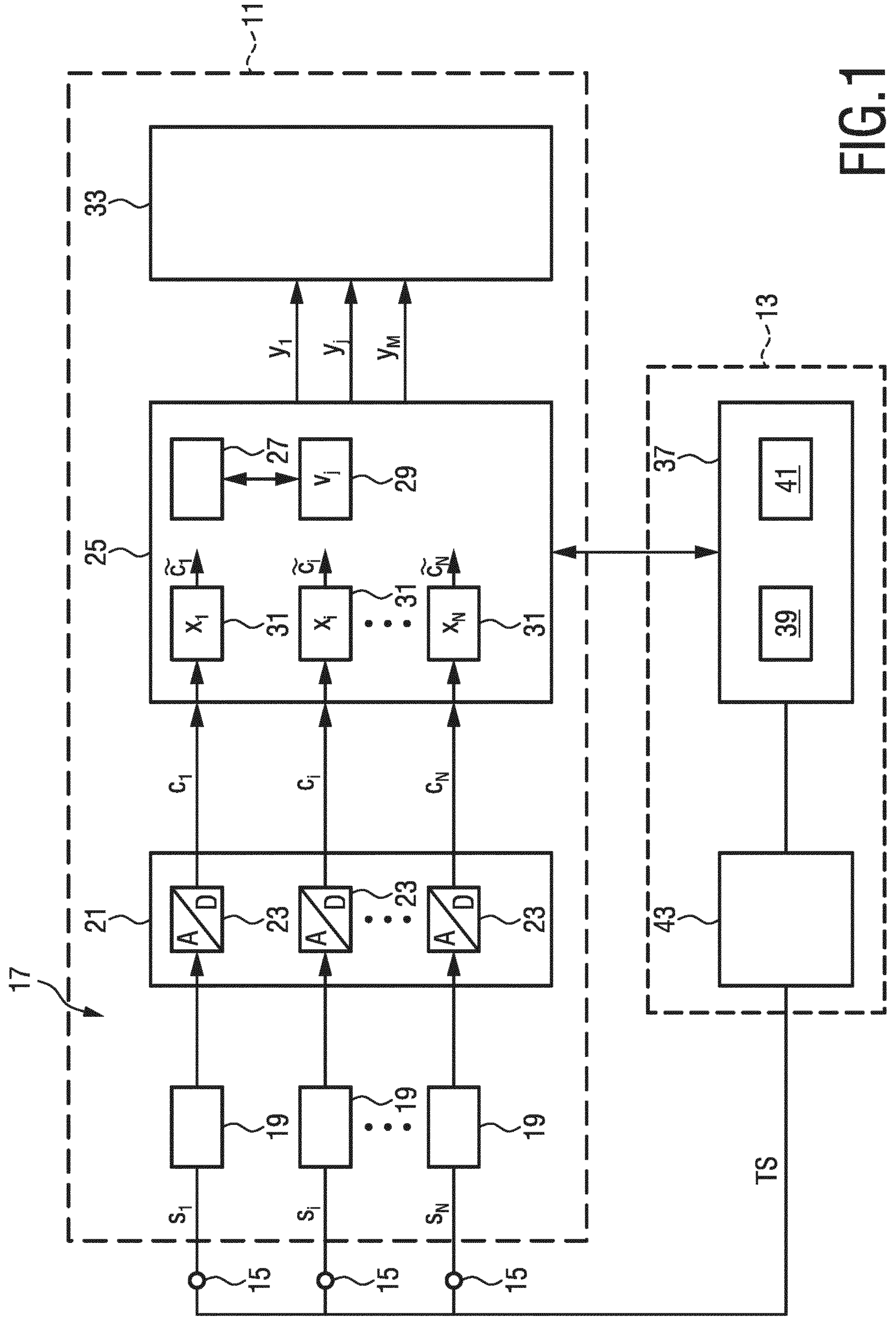
FIG. 1 shows a block diagram of a physiological measurement device and a calibration device.

FIG. 1 shows a physiological measurement device 11 connected to a calibration device 13. The physiological measurement device 11 has multiple channels. For the sake of simplicity, only three channels are shown in FIG. 1 but in general N channels may be present. Each channel has an analog input 15 for inputting an analog input signal $s_i$ i=1, . . . , N. The inputs 15 of the individual channels are connected to an analog front end 17. The analog front end 17 includes analog input circuitry 19 associated with the individual channels. The analog input circuitry 19 may comprise one or more amplifiers, an impedance converter, an analog filter, or the like. The input circuitry of the individual channels is connected to a multichannel analog to digital converter 21. The multichannel analog to digital converter 21 is configured to convert the individual input signals $s_i$ preprocessed by the individual analog input circuitries 19 into samples $c_i$ i=1, . . . , N which represent the input signals $s_i$ of the individual channels. In the shown embodiment, the multichannel analog to digital converter 21 comprises multiple analog to digital converters (ADC 23) where each of these ADCs is associated with a specific channel. In another embodiment, a single ADC 23 may be associated with multiple channels and the multichannel analog to digital converter 21 may comprise a multiplexer to selectively connect one channel to the respective ADC. When using a multiplexer, one ADC 33 may be used to convert the input signal of every channel one after the other. Using the multiplexer, several input channels can be sampled sequentially with one ADC. The here described calibration method may compensate for a timing skew that may present in such a multiplexed setup. In a possible implementation, e.g. an ECG device, two ADCs may be present operable to sample e.g. five ECG input channels sequentially per ADC for a total of ten input channels.

A digital interface of the multichannel analog to digital converter 21 is connected to a processing unit 25 of the measurement device 11 so that the samples $c_i$ of the individual input signals $s_i$ are forwarded to the processing unit 25.

The processing unit 25 may comprise a first processor 27 and a first memory device 29 that constitute a computing device operable to perform various processing steps needed to perform measurements by the physiological measurement device 11. The processing unit 25 comprises multiple digital input filters 31. The number of input filters may correspond to the number N of channels and one digital input filter 31 may be assigned to one specific channel. The individual input filter 31 may be implemented as Finite Impulse Response (FIR) filters having filter coefficients represented by column vectors $x_i$ i 1, . . . , N. A length K of the individual vectors $x_i$ corresponds to the number of filter coefficients of each digital filter 31. The digital filters 31 are also referred to as Input Channel Specific digital Filters (ICSFs) because they are applied to the samples $c_i$ of the input signals $s_i$ before differential output signals are derived from these samples.

Note that the present disclosure is not limited to a specific filter topology. Instead of FIR filters other filters like Infinite Impulse Response (IIR) filters may be applied. The filters 31 may be implemented in software, i.e. a computer program stored in the memory device 29 may be programmed so that the first processor 27 executes a filter algorithm based on the filter coefficients $x_i$. The filter coefficients $x_i$ may be stored in a programmable and non-volatile section of the first memory device 29. The processing unit 25 may be accessible by the calibration device 13 so that the calibration device 13 can read the samples $x_i$ and program the filter coefficients $x_i$.

The processing unit 25 is operable for calculating one or more output signals $y_j$ j=1, . . . , M from the samples $c_i$ of the individual input signals filtered by the individual digital input filters 31. The output signals $y_j$, also referred to as vector signals or just to as "vectors", may be calculated by forming a linear combination of filtered samples $\tilde{c}_l$ of multiple channels, thereby performing a differential measurement with respect to at least two input signals $s_i$. This linear combination may be specified by a definition vector $v_j$ of a specific output signal $y_j$, where $1^T*v_{j=0}$ and 1 stands for a column vector of ones, i.e. $1^T=[1, \ldots, 1]$ and "*" denotes the scalar product. The output signal is $y_j=y_j=\tilde{c}_l*v_j$. The linear combination described by the definition vector specifies a differential measurement. The differential measurement may be based on two or more channels. In some applications like ECG or EEG, the vector signals are often also referred to as "leads".

In physiology, voltage measurements are almost always differential. Other physical quantities like pressure or temperature are usually measured as absolute values (e.g. a temperature of 37° C. or an intra-arterial pressure of 100 mmHg), but in some cases, differential measurements can be of interest (cardiac output can be measured by thermodilution, which requires measuring the temperature difference at two points in a blood vessel). The here described technology can thus be applied to differential measurements that are not voltage measurements, too.

For the sake of simplicity, FIG. 1 shows only one digital filter 31 per input channel. However, it is possible to provide multiple digital filters 31 for one input channel i, each of them processing the samples $c_i$. The different digital filters 31 may be associated with different output signals. Accordingly, a specific variant of the filtered signal $\tilde{c}_l^j$ may be used for calculating a certain output signal $y_j$.

The measurement device 11 may comprise an output device 33 coupled with the processing unit 25 so that the output device 33 can output the output signals $y_j$. For example, the output device 33 may include elements for visualizing the output signals $y_j$, for example a display or a printer. One or more post-processing steps may be present for processing at least one output signal $y_i$ before outputting it by the output device 33.

The physiological measurement device 11 may be an electrophysiological measurement device such as an ECG or an EEG. Various configurations, in particular regarding the number N of channels and the number M of output signals are possible.

A comparatively simple example is an ECG or EEG device having a single output signal (single vector) and two electrodes connected to two inputs 15 (two channels). The only definition vector needed for such a measurement device 11 may be $v_1=[1,-1]$.

Figure 2:
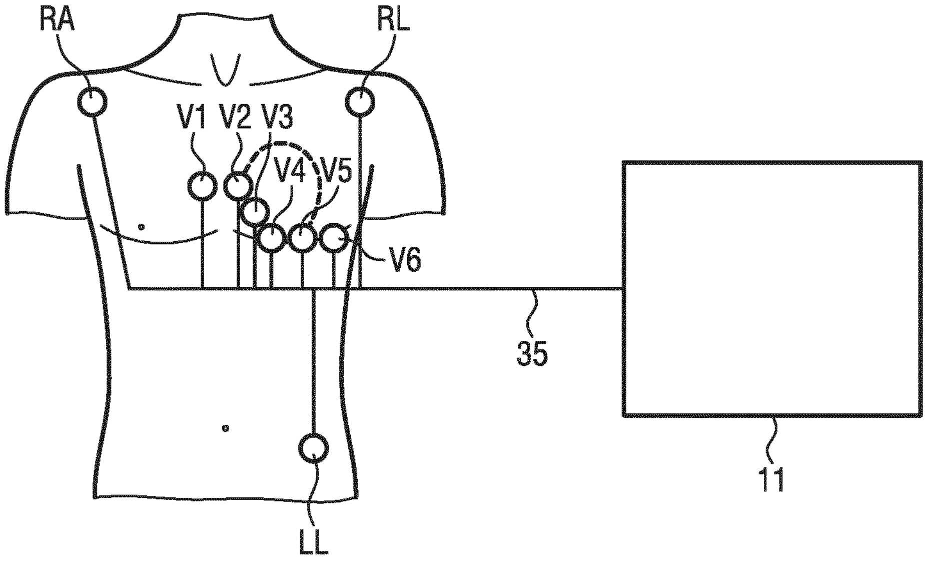
FIG. 2 shows an exemplary measurement device.

According to another example shown in FIG. 2, a 12-lead ECG is provided having nine measurement electrodes connected to N=9 inputs 15 of the measurement device 11. Such measurement device thus has nine channels. The electrodes may include three limb electrodes (right arm RA, left arm LA, left leg LL), six chest electrodes (V1-V6), which are connected via a measurement cable 35 to nine different inputs 15 of the physiological measurement device 11.

The output vector signals $y_1, \ldots, y_2$ may be defined according to twelve leads visualized by means of the output device 33 to medical personnel. The leads and respective vector signals include lead I (LA-RA), lead 11 (LL-RA), lead III (LL-LA), aVR (RA-0,5*(LA+LL)), aVL (LA-0,5*(RA+LL)), aVF (LL-(RA+LA)), and (Vn-WCT); n=1, . . . , 6. WCT corresponds to the Wilson's central terminal voltage which is approximated as (RA+LA+LL)/3.

The present disclosure is not limited to the above two exemplary measurement devices. For example a 15-lead or an 18-lead ECG can be provided based on the present disclosure as well. It is also possible to provide a high-density EEG based on the present disclosure having 32 or more channels.

Figure 3:
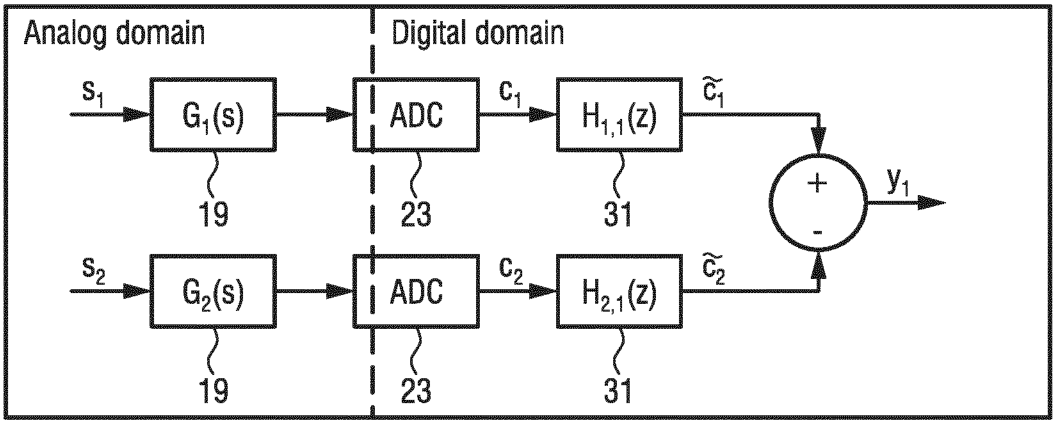
FIG. 3 shows a signal flow within the measurement device according to an embodiment.

FIG. 3 shows an example where an output signal $y_i$ is generated by subtracting a filtered input signal $s_2$ from another filtered input signal $s_i$ (definition vector [1, −1]). Accordingly, the output signal $y_1$ corresponds to a signal obtained by differential measurement based on the two input signals $s_1$ and $s_2$. When performing physiological measurements, the input signals $s_1$, $s_2$ are subject to common mode interference. In an ideal situation, subtracting the two signals $s_1$, $s_2$ from each other would eliminate the common mode part entirely. However, in practical implementation of the measurement device 11, the signal $y_1$ includes a common mode part to some extent due to differences of electrical characteristics e.g. of components 19, 21, 23 of a signal path related to the individual channels.

In electrophysiology voltages are measured that occur between points on the surface of a patient due to activity of muscle cells or nerve cells. The signals of interest are usually in the microvolt (EEG) to millivolt (ECG) range, while the common-mode component of the signal can be tens or hundreds of millivolts. In a medical context, there are many possible sources of interference (including common mode interference) ranging from other pieces of medical equipment, electronic communication or networking devices and power line noise. In order for the output signal $y_j$, to be useful for diagnosis and therapy, electrophysiological measurement devices 11 are required to have a high common mode rejection ratio (CMRR). Although there are standardized test procedures for determining the CMRR in the range of power line frequency of 50 Hz or 60 Hz, common-mode interference should also be mitigated at other frequencies. The frequencies where common-mode interference should be mitigated may include frequencies outside the ECG/EEG bands, especially if the recording device performs some kind of out-of-band processing (for example for electrode impedance measurement or ECG pacemaker pulse detection).

To mitigate common-mode interference, the digital filters 31 may be designed such that a common-mode part of the respective output signals $y_j$ is minimized. To this end the calibration device 13 shown in FIG. 1 can be applied to determine the filter coefficients $x_i$ so that the common-mode component of the individual output signals $y_j$ are minimized. The calibration device 13 comprises a further processing unit 37 including a second processor 39 and a second memory device 41. The further processing unit 37 includes Input/Output (IO) circuitry configured for coupling the further processing unit 37 with a test signal generator 33 of the calibration device 13. The IO circuitry is configured to access the first memory device 29, in particular the non-volatile section thereof, so that the calibration device 13 can read the samples $x_i$ and program the filter coefficients $x_i$. The IO circuitry is configured for performing IO operations to access data present in the measurement device 11 and/or to control the measurement device to carry out a herein described calibration method 45. The further processing unit 37 is coupled with the test signal generator 33 of the calibration device 13. The test signal generator 43 can be controlled by the processing unit 37, via the IO circuitry, to generate a test signal TS fed into the individual inputs 15 of the calibration device when performing a calibration method. A computer comprising the further processing unit 37 may be programmed to perform a herein described method for calibrating the physiological measurement device 13. A respective program can be stored e.g. in the first memory device 13.

Figure 4:
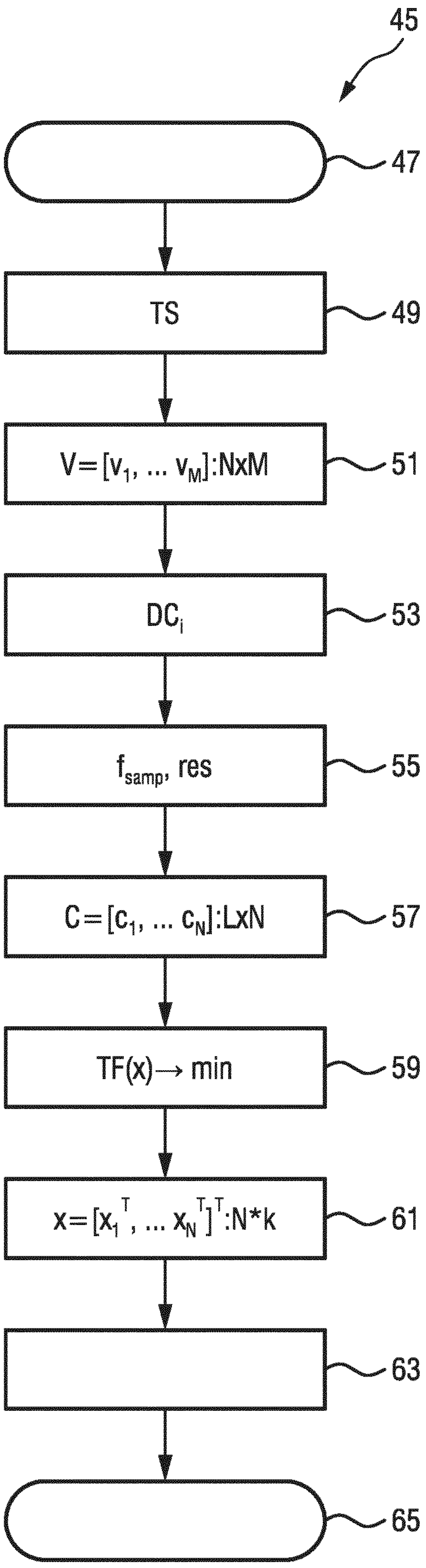
FIG. 4 shows a flow chart of a calibration method.

FIG. 4 shows a method for calibrating the physiological measurement device 11. The method 45 may be carried out by the calibration device 13. Accordingly, the further processing unit 37 can be configured to execute the method 45. In particular, the second memory device 41 may include a computer program that is programmed to execute the method 45 when run on a computer such as the further processing unit 37. Alternatively, at least some operations of the method 45 may carried out by the measurement device 11, in particular the processing unit 25.

The method 45 may be executed as a part of a production final test related to the measurement device 11. During the production final test, or in general when performing a calibration, the calibration device 13 is connected to the measurement device 11. There may be an electrical connection between the test signal generator 43 and the inputs 15 configured for applying the test signal TS to the inputs 15 and a communication connection between the processing unit 37 of the calibration device and the processing unit 25 of the measurement device configured for reading the samples $c_i$ and for writing back the filter coefficients $x_i$ calculated by the calibration device 13 as described below.

After a start 47 of the method 45, the test signal TS is applied to the inputs 15 in step 49. To this end, the further processing unit 37 may control the test signal generator 43 to output the test signal TS. The test signal should cover the frequency range of interest of the measurement device and the amplitude should be large enough to cover a significant part of the measurement devices ADCs 23 input range in order to minimize error due to quantization. Different types of signals can be used subsequently, for example chirp or sweep signals, pulse train signals, periodic signals with sharp transitions like square or saw tooth waves, or even wide or band-limited noise.

In a step 51, the method 45 inputs or otherwise determines one or more definition vectors $v_1, \ldots, v_M$, which may correspond to the leads supported by the measurement device 11. As shown in FIG. 4, the definition vectors can be arranged in a matrix $V=[v_1, \ldots, v_M]$.

Step 53 of the method 45 inputs at least one DC gain value $DC_i$ of a specific channel i. The DC gain values $DC_i$ may be determined in a separate measurement procedure, which may be carried out during the production final test, and describe the gain at frequency 0 within a specific channel, in particular within the analog circuitry 19 of that channel.

In a step 55 of the method 45 a sampling frequency $f_{SAMP}$ and a resolution res of the ADCs 23 are configured by the calibration device 13. The sampling rate $f_{SAMP}$ may be increased compared to a sampling rate used during normal operation of the measurement device 11. The resolution res used during the calibration method 45 may be reduced compared to a resolution used during normal operation. For example, the sampling rate during calibration may be at least 2000 Hz, wherein a typical ECG recorder usually operates at sampling rates between 500 Hz and 2000 Hz when performing ECG measurements. To configure the special sampling rate and resolution during the calibration, the measurement device, in particular the multichannel analog digital converter 21 and/or the processing unit 25 may be switched to a special operating mode.

While the test signal TS is applied, the measurement device 11 records the unfiltered ADC samples $c_i$ of all input channels. In step 57, the method 45 receives the samples $c_1, \ldots, c_N$ related to the individual channels and representing the test signal TS distorted by the analog front end 17. As shown in FIG. 4, the samples may be represented by an L×N matrix $C=[c_1, \ldots, c_N]$. L is the number of recorded samples.

The recorded samples C and the definition vectors V may be used to establish an optimization problem to minimize a target function TF in step 59. The target function TF may depend on an output vector X including at least some, preferably all, filter coefficients $x_i$. The filter coefficients may be represented by a column vector $X=[x_1^T, \ldots, x_{NT}^T]^T$ which has a length of N*K elements, K corresponding to the number of filter coefficients per channel. Accordingly, all filters 31 of the shown embodiment have the same number of coefficients. However, the individual filters 31 may also differ in terms of number of coefficients and the calibration method 45 may be adapted accordingly.

In general, when considering cases of more than one digital filter 31 per channel, the length of the coefficient vector X is 1 . . . imax, N≤imax≤N*M. The minimum value for imax represents the case of only one matching filter per input channel, and the maximum value represents the case of one matching filter per input channel and possible output vector. Without loss of generality, the following will assume that imax=N.

The target function TF may include a convex or quasi-convex penalty function, in particular a norm, preferably the L-infinity norm (maximum norm). Other norms like the L2 norm (Euclidean norm) can be used as well. The optimization problem to be solved in step 59 is comparatively large due to the number of samples but can be handled with existing solvers for optimization problems.

An argument of the target function may include the unfiltered samples $c_i$, the definition vectors $v_j$ and the filter coefficients $x_i$. The filter coefficients $x_i$ are target variables to be determined during optimization. Based on the optimization optimal or suboptimal values of the filter coefficients are obtained as a result of the optimization. The optimization may comprise applying a numerical solver for optimization problems.

The argument of the target function may comprise a column vector of all samples of the vector signal and can be formally modelled as follows.

$$Y = \begin{bmatrix} C_{v1} \\ \ldots \\ C_{vM} \end{bmatrix} \cdot x$$

where $To(c_i)$ is the Toeplitz matrix of ci elements, size (L−K+1, K). The first column contains the last (L−K+1) elements of ci; the first row contains the first K elements of ci in reverse order. Example for c=[1 2 3 4 5 6 7 8 9]T, L=9, K=4:

$$To(c) = \begin{bmatrix} 4 & 3 & 2 & 1 \\ 5 & 4 & 3 & 2 \\ 6 & 5 & 4 & 3 \\ 7 & 6 & 5 & 4 \\ 8 & 7 & 6 & 5 \\ 9 & 8 & 7 & 6 \end{bmatrix}$$

CA=[To(c1) To(c2) . . . To(cN)] is augmented input sample matrix for convenient calculation of all output samples. CA can also be constructed from Hankel matrices; this merely changes the order of elements and hence the order of the matching filter coefficients in the output.

⊙ is the Hadamard (element-wise) matrix product

⊗: Kronecker product $$C_{vi} = C_A \odot \left(v_i^T \otimes 1_{L-K+1,K}\right):$$

Sample matrix that only retains input channel samples used in vector i, multiplied by the appropriate sign and coefficient. Note the use of Hadamard/element-wise product and Kronecker product.

$C_{vi} \cdot X$ is a column vector of output samples of vector signal i

Based on the target function argument, the optimization can be formulated as a multi-objective optimization: Minimize 1-infinity norm of the vector of output samples and also minimize another norm (or norm-like penalty function like the Huber loss function that has the robust behavior to outliers of the 11-norm while being a smooth function which the 11-norm is not), usually the 12-norm of the output sample vector (with lower priority), i.e., $$\text{minimize } \|Y\|_\infty, \|Y\|_2 \text{ with regard to } X.$$

In general, the optimization problem should minimize the 1-infinity norm (i.e. the maximum absolute deviation from zero when a pure common-mode signal is applied to the inputs) if the subsequent processing of the differential signal is sensitive to outliers (e.g. pace pulse detection in ECG) instead of signal energy. However, some 1-infinity norm optimality can be traded for finding a solution that has a small 12-norm (or norm other than 1-infinity). Depending on the used solvers, the solution of the 1-infinity norm optimization might already be biased towards also minimizing other norms. If this is not the case, the multi-objective optimization problem can either be scalarized to $$\text{minimize } \|y\|_\infty + \gamma\ \|y\|_2 \text{ with regard to } X$$

or it can be split into a first 1-infinity norm optimization, followed by the minimization of a different norm while keeping the 1-infinity norm constant (possibly allow some deviation from the value of the first optimization to simplify the job of the optimization algorithm).

The optimization problem may include constraints. For example, a linear equality constraint of the form $1^T*x_i=b_i$ can be applied in order to compensate differences between the individual channel as regards the DC gain. The value b; may be derived from the DC gain values $DC_i$ obtained in step 53. Similarly, the gain of at least one digital filter 31 at the Nyquist frequency can be constraint using a linear equality constraint.

At least one non-linear equality constraint may be applied to the optimization problem, e.g. to constrain the gain of a digital filter 31 to be equal to a value $b_i$. This constrain has the form $(\sin f^T*x_i)^2+(\cos f^T*x_i)^2=(b_i)^2$. This type of constraint can also be formulated using complex exponentials instead of real valued vectors of sine and cosine values. In this case, scalar products may be used to produce real-valued output.

Moreover, a non-linear inequality constraint may be applied to the optimization problem, e.g. in order to constrain the gain of at least one of the digital filters 31 at a given frequency to be equal or less than a value $b_i$. This constraint has the form $(\sin f^T*x_i)^2+(\cos f^T*x_i)^2\leq(b_i)^2$. This type of constraint can also be formulated using complex exponentials instead of real valued vectors of sine and cosine values. In this case, scalar products may be used to produce real-valued output.

Bound constraints, which are a special case of linear inequality constraints, may be applied to constrain values of coefficients of the individual digital filters 31. These constraints have the form $b_{min}\leq x\leq b_{max}$. These constraints can be used to avoid numeric overflows when storing the coefficients and to avoid numeric overflows when calculating the filter output. Moreover high-pass behavior of the individual filters 31 may be limited.

A further constraint $\|\|\|x_i\|b_i$ related to a norm calculated from the coefficients $x_i$ may be applied. The norm may be the 12-norm of the filter coefficients. Such constraints limit the average gain of the filters and the amount of high pass behavior of the filter. This constraint corresponds to a non-linear convex inequality constraint.

The present disclosure is not limited to the above described constraints applied to the optimization problem. Other types of constraints may also be included, for example constraining the value of at least some coefficient vector $x_i$ to have decreasing magnitudes, which forces the filter to be closer to a minimum-phase (and minimum-delay) system.

The optimization problem can be varied, e.g. to reduce its computational complexity. One approach is splitting the optimization problem into sub-problems than are, in sum, smaller than the original problem. For example, in an ECG application, the calibration could first calculate the matching filter coefficients for the vectors formed by limb leads (I, II, III, aVR, aVL, aVF), and then, keeping the first set of coefficients constant, calculate the coefficients for each chest electrode individually (as no vectors with two chest electrodes are used in practice, the chest electrode filter coefficients can be calculated individually for each chest electrode). This results in seven smaller optimization problems.

Alternatively, the calculation of the Wilson's Central Terminal (WCT) vector signal (RA+LA+LL)/3 could use its own coefficients, in which case the filter coefficients of channels related to chest electrodes V1, . . . , V6 must be matched simultaneously (i.e. during one optimization run) as they all require the WCT. Calculating filter coefficients specially for the WCT vector signal splits the original problem into two smaller sub-problems—one optimization run for the limb lead vector signals RA, LA, LL and one optimization run for the chest lead vectors V1, . . . , V6.

When using multiple matching filters per electrode, the optimization problem can be split into entirely independent sub-problems that can each be solved individually without adversely affecting the overall optimality of the total solution.

After completion of the optimization run(s), step 61 of the method 45 obtains the filter coefficients X of the individual digital filters.

The obtained filter coefficients X may be stored, in step 63, into an appropriate storage region of the first memory device 29 of the measurement device.

In step 65, the method 45 is terminated.

Figure 5:
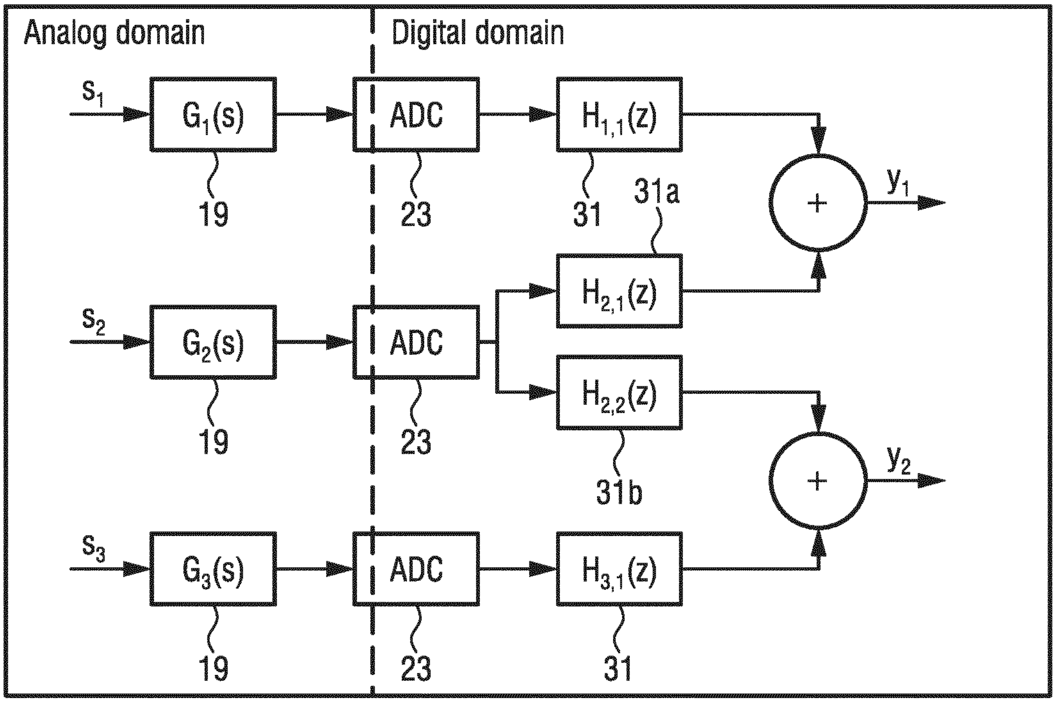
FIG. 5 shows a further signal flow within the measurement device according to an embodiment.

In one embodiment, each channel has exactly one digital filter 31 the filter samples $\tilde{c}_l$ generated by these filters 31 is used to calculate every output signal $y_j$ corresponding to a specific vector or lead. In a different embodiment illustrated in FIG. 5 at least one channel has at least two sets of filter coefficients corresponding to different digital filters 31*a*, 31*b*. These filters may be used to calculate one or more specific output values. In the example shown in FIG. 5 the digital filter 31*a* is used to calculate the output signal $y_i$ and the digital filter 31*b* is used to calculate the output signal $y_2$. Both digital filters 31*a*, 31*b* are configured to filter the input signal $s_2$ of one channel. In an embodiment, each output signal $y_j$ has a dedicated set of digital filters 31. In other words, the set of filter coefficients corresponding to the individual digital filters 31 are obtained for a specific vector corresponding to the output signal $y_j$.

To sum up, the present calibration method obtains filter coefficients of the digital filters 31 by means of optimization of a target function based on both samples of a test signal applied to inputs 15 of different channels as well as the definition vectors. This allows for determining the filter coefficients directly without selecting a reference signal. Moreover, constraints related to characteristics of the filters 31 that have nothing to do with common-mode interference mitigation can easily be incorporated into the calibration method. The calibration method 45 may be used in combination with measurement devices 11 that filter the sampled input signal $s_i$ in the digital domain and then calculate the vector signals from the filtered samples corresponding to a filtered input signal. Moreover, a measurement device 11 is described that comprises more than one digital input filter 31 associated with a certain channel. The digital input filters 31 associated with the same channel may be associated with different vector signals.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A method for minimizing common mode interference in a physiological measurement device, the method comprising:

- receiving samples ($c_i$) of multiple input signals ($s_i$) of the measurement device corresponding to a test signal (TS) applied to multiple input channels of the measurement device wherein the samples ($c_i$) are received with a calibration sampling rate ($f_{samp}$) that is increased compared to an operating sampling rate applied to perform physiological measurements by the measurement device;
- inputting at least one definition vector ($v_i$) describing a linear combination of samples ($c_i$) of at least two input channels;
- optimizing a metric calculated from at least one vector signal ($y_i$), the vector signal being based on the samples ($c_i$) of at least two of the received input signals and the definition vector ($v_i$); and
- based on the optimizing, obtaining at least one set of filter coefficients ($x_i$) for at least one digital input filter associated with a specific input channel;
- storing the at least one set of filter coefficients in a memory device of the physiological measurement device;
- filtering samples of one input signal with the at least one digital input filter according to the stored at least one set of filter coefficients to obtain filtered samples of this input signal for physiological measurement; and
- calculating at least one vector signal from multiple filtered input signals based on the at least one definition vector, wherein a common-mode part of the at least one vector signal is minimized.

2. The method of claim 1, wherein multiple definition vectors ($v_i$) are inputted and at least one set of filter coefficients ($x_i$) is obtained for a specific input vector ($v_i$).

3. The method of claim 1, wherein optimizing the metric comprises multiple optimizing steps, a set of filter coefficient obtained by one step being kept as constant for a subsequent optimizing step.

4. The method of claim 1, wherein the optimizing is subject to at least one linear equality constraint with respect to a filter coefficient ($x_i$).

5. The method of claim 4, wherein the method comprises inputting a DC gain value of at least one input channel and determining a corresponding linear equality constraint based on the DC gain value ($DC_i$).

6. The method of claim 1, wherein the optimizing is subject to at least one nonlinear inequality constraint for limiting a gain of a certain input filter at a given frequency.

7. The method of claim 1, wherein the optimizing is subject to at least one bounds constraint with respect to filter coefficients ($x_i$).

8. The method of claim 1, wherein a calibration resolution (res) of the received samples ($c_i$) differs from a measurement resolution of samples received to perform the physiological measurements.

9. The method according to claim 1, wherein optimizing the metric comprises minimizing a penalty function of output samples ($y_i$), the output samples corresponding to at least one vector signal ($y_i$) calculated from the input signal filtered according to the filter coefficients ($x_i$) and from the definition vector ($v_i$).

10. The method of claim 9, wherein optimizing comprises minimizing multiple different penalty functions of the output samples ($y_i$) simultaneously or minimizing a scalar target function of different penalty functions.

11. The method of claim 9, wherein at least one penalty function is a convex or quasi-convex penalty function.

12. The method of claim 11, wherein the penalty function is a norm.

13. A computer program comprising program code means for causing a computer to carry out the steps of the method as claimed in claim 1 when said computer program is carried out on the computer.

14. A calibration device for minimizing common mode interference in a physiological measurement device, the calibration device comprising a processor configured to:

- receive samples ($c_i$) of multiple input signals ($s_i$) of the measurement device corresponding to a test signal (TS) applied to multiple input channels of the measurement device. wherein the samples are received with a calibration sampling rate ($f_{samp}$) that is increased compared to an operating sampling rate applied to perform physiological measurements by the measurement device;
- input at least one definition vector ($v_i$) describing a linear combination of samples ($c_i$) of at least two input channels;
- optimize a metric calculated from at least one vector signal (yi), the vector signal being based on the samples ($c_i$) of at least two of the received input signals and the definition vector ($v_i$);
- based on the optimizing, obtain at least one set of filter coefficients (xi) for at least one digital input filter associated with a specific input channel;

store the at least one set of filter coefficients in a memory device of the physiological measurement device; and wherein the physiological measurement device filters samples of one input signal with the at least one digital input filter according to the stored at least one set of filter coefficients to obtain filtered samples of this input signal for physiological measurement, and a processor of the physiological measurement device calculates at least one vector signal from multiple filtered input signals based on the at least one definition vector, wherein a common-mode part of the at least one vector signal is minimized.

15. A physiological measurement device comprising:

- multiple input channels for processing multiple input signals ($s_i$), wherein during calibration samples of the multiple input signals are received with a calibration sampling rate ($f_{samp}$) that is increased compared to an operating sampling rate applied to perform physiological measurements by the physiological measurement device;
- a memory device configured to store multiple sets of filter coefficients ($x_i$), at least one of said multiple sets being related to at least one digital input filter of the measurement device, the digital input filter being configured to filter samples ($c_i$) of one input signal ($s_i$) to obtain filtered samples of this input signal, and a processor configured to calculate multiple vector signals ($y_i$), one of said multiple vector signals being calculated from multiple filtered input signals based on a definition vector ($v_i$) wherein at least one of said multiple sets of filter coefficients is obtained based on an optimization of a metric calculated from at least one vector signal, the at least one vector signal being based on samples corresponding to a test signal applied to the multiple input channels and the definition vector;

wherein the memory device is configured to store different sets of filter coefficients ($x_i$) related to one input channel and the processor is configured to select one of the different sets of filter coefficients ($x_i$) for calculating a specific vector signal ($y_i$).

* * * * *